United States Patent [19]

Danklmaier et al.

[11] Patent Number: 5,574,155
[45] Date of Patent: Nov. 12, 1996

[54] PROCESS FOR THE SYNTHESIS OF THE DISODIUM SALT HEMIHEPTAHYDRATE OF CEFTRIAXONE

[75] Inventors: Johann Danklmaier, Vomp; Ingolf Macher; Bernhard Prager, both of Wörgl, all of Austria

[73] Assignee: BIOCHEMIE Gesellschaft m.b.H., Austria

[21] Appl. No.: 19,735

[22] Filed: Feb. 19, 1993

[30] Foreign Application Priority Data

Feb. 20, 1992 [AT] Austria .................. 309/92

[51] Int. Cl.⁶ .................. C07D 501/36
[52] U.S. Cl. .................. 540/227
[58] Field of Search .................. 540/227

[56] References Cited

U.S. PATENT DOCUMENTS

| | | | |
|---|---|---|---|
| 4,327,210 | 4/1982 | Montaum et al. | 544/27 |
| 4,758,556 | 7/1988 | Durckheimer et al. | 514/206 |
| 4,767,852 | 8/1988 | Ascher | 540/222 |
| 5,026,843 | 6/1991 | Riccardo et al. | 540/227 |
| 5,126,445 | 6/1992 | Martin | 540/227 |

FOREIGN PATENT DOCUMENTS

| | | |
|---|---|---|
| 1146165 | 5/1983 | Canada . |
| 37380 | 10/1981 | European Pat. Off. . |
| 175814 | 4/1986 | European Pat. Off. . |
| 0553792 | 8/1993 | European Pat. Off. . |
| 3720681 | 1/1988 | Germany . |

OTHER PUBLICATIONS

Chem. Abst. 99, 70458 (1983).

*Primary Examiner*—John M. Ford
*Assistant Examiner*—Pavanaram K. Sripada
*Attorney, Agent, or Firm*—Robert S. Honor; Melvyn M. Kassenoff; Thomas O. McGovern

[57] ABSTRACT

The invention relates to a new process for the production of the disodium salt hemiheptahydrate of ceftriaxone by reacting 7-amino-3-{[(2,5-dihydro-6-hydroxy-2-methyl-5-oxo-1,2,4-triazin-3-yl)thio]methyl}-3-cephem-4-carboxylic acid with 2-(2-aminothiazol-4-yl)-2-syn-methoximinoacetic acid-(2-benzthiazolyl)thiolester in the presence of a base, characterized in that the reaction and the crystallization of the disodium salt hemiheptahydrate of ceftriaxone are carried out in aqueous acetone.

13 Claims, No Drawings

PROCESS FOR THE SYNTHESIS OF THE DISODIUM SALT HEMIHEPTAHYDRATE OF CEFTRIAXONE

New process for the production of ceftriaxone The invention relates to a new economical and simple process for the production of the disodium salt hemiheptahydrate of ceftriaxone of formula I

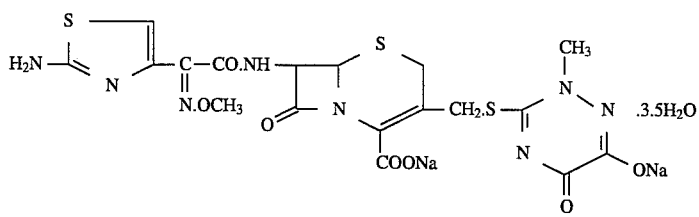

Ceftriaxone is a third generation cephalosporin and is one of the most important parenterally applied antibiotics.

All relevant processes described in literature start with 7-ACT of formula II

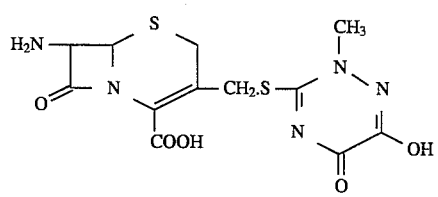

whereby the side chain in N-protected or unprotected form is introduced into the amino group in position 7 using various acylation techniques.

The most elegant method of introducing the side chain uses a reactive thioester, e.g. MAEM of formula III

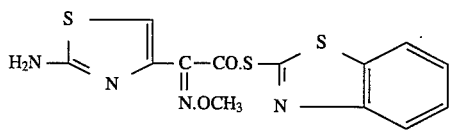

since here it is not necessary to protect the amino function of the 2-aminothiazolyl group. This process was first described in EP-A-0037380, and since then has been used in a few slightly modified processes (e.g. EP-A-0399094).

A further process, which operates without a protecting group at the amino function of the aminothiazole, is described in EP-A-0175814. In this process, active esters with 1-hydroxybenzotriazole are employed. Processes using an amino protecting group are described in GB Patent Application 2 022 090 and in EP-A-0030294. Of all the processes described, the one using activated thioester, as described in EP-A-0037380, appears to be the best. In EP-A-0037380, 7-ACT of formula II is silylated in dichloromethane with N,O-bis-(trimethylsilyl)acetamide and reacted with MAEM of formula III. By adding methanol-containing acetonitrile, the ceftriaxone formed is precipitated as a free acid. This then has to be converted in a further reaction step into the desired form of the disodium salt.

In the process described in EP-A-0037380, not only an ecologically hazardous chlorinated hydrocarbon (dichloromethane) is used as the reaction solvent which is difficult to recycle or dispose of in an environmentally acceptable manner, but also the toxic acetonitrile is employed to isolate the active substance. In this process, a mother liquor is obtained, which consists of a mixture of dichloromethane, methanol, acetonitrile, acetamide and siloxanes. Apart from the ecologically hazardous dichloromethane, this mixture also contains the toxic solvents methanol and acetonitrile, and in addition the suspected carcinogenic acetamide. Regeneration of the individual components from this mixture may only be carried out at very great expense, if at all. A further disadvantage of the process described in EP-A-0037380 is that first of all ceftriaxone has to be isolated, and in an additional step of the process, the disodium salt form thereof which is necessary for parenteral application must be produced.

In the process described in EP-A-0399094, the reaction of 7-ACT with MAEM is effected in a mixture of dimethylacetamide, tetrahydrofuran and water. In order to be able to isolate a product of high purity, in this process first of all the N,N-dibenzylethylenediamine salt of ceftriaxone must be produced. For this, two further solvents are employed, namely ethyl acetate and dichloromethane, so that the mother liquor to be regenerated is finally a mixture of 5 different solvents, containing again the ecologically hazardous dichloromethane. Finally, in order to produce the desired ceftriaxone disodium salt hemiheptahydrate, acetone is required. In this process, the result is thus a mixture of solvents, the regeneration of which into pure individual components in an economical manner is not possible. In addition, two isolation steps are necessary to obtain the desired product.

There was thus a clear need to find an alternative industrially viable process for the production of the compound of formula I. Surprisingly we have found a new, substantially simplified process for the production of the compound of formula I.

In accordance with the invention, the disodium salt hemiheptahydrate of ceftriaxone of formula I is obtained, by reacting 7-ACT of formula II with MAEM of formula III in aqueous acetone in the presence of a base. Suitably the base employed is either a tertiary amine, e.g. a trialkylamine, such as triethylamine, 2, 3-or 4-picoline, 2,6-lutidine, 1,4-dimethylpiperazine, N-ethylpiperidine or N-methylmorpholine, preferably triethylamine, or a sodium-containing base, such as sodium hydroxide, sodium hydrogen carbonate or sodium carbonate, especially sodium hydroxide.

The reaction temperature is suitably from 0° to 50° C., preferably from 10° to 25° C., in particular 15° to 20° C., when a tertiary amine is employed as a base. When a sodium-containing base is employed, the reaction temperature lies suitably between 0° and 50° C., preferably between 20° and 40° C., more preferably between room temperature and 30° C.

After completion of the reaction, the product is brought to crystallization, optionally by adding further acetone, and is subsequently isolated and dried. When a tertiary amine is used as the base, at the end of the reaction, a source of sodium ions in the form of sodium hydroxide, sodium acetate or sodium 2-ethylhexanoate is added to the reaction mixture to crystallize the disodium salt hemiheptahydrate of ceftriaxone, whereby the addition is made in solid form, or in the form of an aqueous or acetonic or aqueous-acetonic solution.

The compound of formula III is known and may be produced by the process disclosed in EP-A-0037380.

The process of the present invention offers numerous advantages over the processes of the prior art.

In the process according to the invention, regeneration of the single solvent used, acetone, (apart from water), is very simple, especially if a sodium-containing base is used in the reaction, because in this case a simple rectification of the mother liquor is sufficient to regenerate the acetone in re-usable form. When using a tertiary amine, e.g. a trialkylamine in the reaction, regeneration both of the acetone and of the base is similarly very simple. The acetone may be regenerated from the mother liquor by rectification after adding an acid, e.g. sulphuric acid, whereby the tertiary amine forms a salt. Afterwards, the tertiary amine may be released with an inorganic base, e.g. sodium hydroxide, and recovered by distillation.

In the process according to the invention, no chlorinated hydrocarbons are used, no silylation step is necessary, and also no further toxic solvents are required to isolate the product. In the process according to the invention, apart from water, the only solvent used is the ecologically substantially acceptable acetone. Thus also no mother liquors are obtained, which are made up of many solvents and are thus difficult to regenerate.

The process is very simple, since no protecting groups are required, both the reaction and the crystallization may be effected in the same reaction vessel, and no expensive separation techniques, such as extraction or isolation of intermediates are necessary. Using the process according to the invention, the desired disodium salt hemiheptahydrate of ceftriaxone is obtained directly, that is without having to isolate the free acid (ceftriaxone) or any other salt. The product is isolated from the reaction mixture directly in highly pure form and high yield. The process according to the invention thus offers great ecological and economical advantages, since execution of the reaction, including product isolation, working-up of mother liquors and regeneration of solvents, is very simple, and no ecologically hazardous and/or toxic solvents are used.

Apart from all these technical, ecological and economical advantages of the process according to the invention, excellent yields and very good quality of the desired product ceftriaxone disodium salt hemiheptahydrate are also obtained. The process is suitable for industrial scale.

The following Examples illustrate the invention more fully, without limiting its scope. All temperatures are given in degrees Centigrade.

7-{[2-(2-Aminothiazol-4-yl)-2-Syn-Methoxy-imino]acetamido}-3-{[(2,5-dihydro-6-hydroxy-2-methyl-5-oxo-1,2,4-triazin-3-yl)Thio]Methyl}-3-Cephem-4-Carboxylic Acid Disodium Salt Hemiheptahydrate (compound of formula I)

Example 1

37.1 g of 7-amino-3-{[(2,5-dihydro-6-hydroxy-2-methyl-5-oxo-1,2,4-triazin-3-yl)thio]methyl}-3-cephem-4-carboxylic acid (7-ACT) and 37.8 g of 2-(2-aminothiazol-4-yl)-2-synmethoxyiminoacetic acid-(2-benzthiazolyl)thiolester (MAEM) are suspended in a mixture of 100 ml of water and 400 ml of acetone. A total of 32.5 ml of triethylamine is added dropwise at such a rate to the stirred suspension which is cooled to 15°, that the pH value does not exceed 8. The solution is stirred at this temperature until the reaction is completed, and subsequently mixed with 28.4 g of sodium acetate trihydrate in 60 ml of water. The cloudy solution is seeded and stirred for 30 minutes at room temperature. Afterwards, 1420 ml of acetone is added dropwise within one hour and the resulting crystal suspension is stirred for a further 30 minutes. The deposit is filtered off, washed with 100 ml each of acetone/water=8/2, acetone/water=9/1 and acetone, and dried in a vacuum drying chamber. 59.8 g (90.4%) of the title compound are obtained with 99.7% purity.

Example 2

The reaction is carried out as described in Example 1, except that the reaction temperature is 20° and crystallization is effected by adding 60 ml of water and 34.9 g of sodium 2-ethylhexanoate instead of the sodium acetate solution. 59.2 g (88.9%) of the compound of formula I are obtained with 98.8 % purity.

Example 3

18.6 g of 7-ACT and 19.3 g of MAEM are suspended in a mixture of 50 ml of water and 150 ml of acetone. A total of 55 ml of 2 N sodium hydroxide solution is added dropwise to the stirred suspension at 25° at such a rate, that the pH value does not exceed 8. After the reaction is completed, 600 ml of acetone are added dropwise within 90 minutes. The crystal suspension is stirred for a further 1 hour. The deposit is filtered off, washed with 100 ml each of acetone/water=8/2, acetone/water=9/1 and acetone, and dried in a vacuum drying chamber. 29.1 g (88%) of the compound of formula I are obtained with 97.7% purity.

Example 4

100 ml of a saturated sodium hydrogen carbonate solution is added over 15 minutes to a stirred suspension of 18.6 g of 7-ACT in a mixture of 50 ml of acetone and 50 ml of water. After 1 hour stirring at room temperature, 100 ml of acetone and 19.3 g of MAEM are added to the clear solution. The reaction mixture is maintained at 25° until completion of the reaction. Afterwards, the mixture is crystallized and worked up as described in Example 3. 29.2 g (88.3%) of the compound of formula I are obtained with 98.8% purity.

Example 5

The reaction is carried out as described in Example 4. 5.8 g of sodium carbonate in 55 ml of water are used as the base instead of the sodium hydrogen carbonate solution. 29.7 g (89.8%) of the compound of formula I are obtained with 99.6% purity.

Example 6

A suspension of 18.6 g of 7-ACT and 18.9 g of MAEM in a mixture of 50 ml of water and 200 ml of acetone is cooled to 15°. The suspension is stirred and treated dropwise with 12.8 ml of N-methylmorpholine in such amanner that the pH value does not exceed 7. After completion of the reaction, 50 ml of water are added, whereby a clear solution is obtained. 14.2 g of sodium acetate and 30 ml of water are added to this solution. Then the product is crystallized by adding acetone (in all ca. 1400 ml). Stirring is effected for 45 minutes, and then the deposit is filtered off. The product is washed and dried as described in Example 3. 28.7 g (86.8%) of the compound of formula I are obtained.

We claim:

1. A process for synthesizing the disodium salt hemiheptahydrate of ceftriaxone comprising (i) reacting the compound of the formula

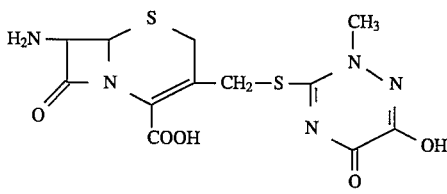

with the compound of the formula

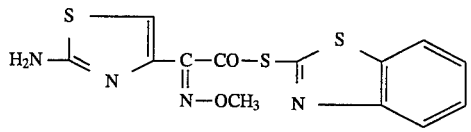

in aqueous acetone in the presence of an organic base that does not contain sodium ions, (ii) adding a source of sodium ions, and (iii) adding additional acetone to precipitate the disodium salt hemiheptahydrate of ceftriaxone.

2. A process according to claim 1 wherein the organic base that does not contain sodium ions is a tertiary amine.

3. A process according to claim 2 wherein the tertiary amine is triethylamine, 2-, 3- or 4-picoline, 2,6-lutidine, 1,4-dimethylpiperazine, N-ethylpiperidine or N-methylmorpholine.

4. A process according to claim 3 wherein the tertiary amine is triethylamine or N-methylmorpholine.

5. A process according to claim 4 wherein the tertiary amine is triethylamine.

6. A process according to claim 5 wherein the source of sodium ions is sodium hydroxide, sodium acetate or sodium 2-ethylhexanote.

7. A process according to claim 6 wherein Step (i) is carried out at 0°–50° C.

8. A process according to claim 7 wherein Step (i) is carried out at 10°–25° C.

9. A process according to claim 8 wherein Step (i) is carried out at 15°–25° C.

10. A process according to claim 2 wherein the source of sodium ions is sodium hydroxide, sodium acetate or sodium 2-ethylhexanote.

11. A process according to claim 10 wherein Step (i) is carried out at 0°–50° C.

12. A process according to claim 11 wherein Step (i) is carried out at 10°–25° C.

13. A process according to claim 12 wherein Step (i) is carried out at 15°–25° C.

* * * * *